(12) United States Patent
Chewter et al.

(10) Patent No.: US 8,569,525 B2
(45) Date of Patent: Oct. 29, 2013

(54) PROCESS FOR PRODUCING ETHYLENE OXIDE

(75) Inventors: Leslie Andrew Chewter, Amsterdam (NL); Herve Henry, Rotterdam (NL); Jeroen Van Westrenen, Amsterdam (NL)

(73) Assignee: Shell Oil Company, Houston, TX (US)

(*) Notice: Subject to any disclaimer, the term of this patent is extended or adjusted under 35 U.S.C. 154(b) by 301 days.

(21) Appl. No.: 12/942,864

(22) Filed: Nov. 9, 2010

(65) Prior Publication Data
US 2011/0137053 A1 Jun. 9, 2011

(30) Foreign Application Priority Data

Nov. 10, 2009 (EP) ..................................... 09175604

(51) Int. Cl.
*C07D 301/03* (2006.01)
(52) U.S. Cl.
USPC ......................................................... 549/523
(58) Field of Classification Search
USPC ......................................................... 549/523
See application file for complete search history.

(56) References Cited

U.S. PATENT DOCUMENTS

| | | | | |
|---|---|---|---|---|
| 3,140,153 A | * | 7/1964 | Huckins, Jr. ................... | 423/351 |
| 3,761,538 A | | 9/1973 | Espino et al. | |
| 4,455,394 A | | 6/1984 | Pinto ............................. | 518/704 |
| 4,536,606 A | | 8/1985 | Hobbs ........................... | 585/650 |
| 4,565,803 A | | 1/1986 | Schoenthal et al. ........... | 502/303 |
| 4,666,945 A | | 5/1987 | Osugi et al. ................... | 518/713 |
| 4,695,560 A | | 9/1987 | Gattuso et al. ................ | 502/222 |
| 5,045,520 A | | 9/1991 | Curry-Hyde et al. ......... | 502/301 |
| 5,254,520 A | | 10/1993 | Sofianos ........................ | 502/307 |
| 5,385,949 A | | 1/1995 | Tierney et al. ................ | 518/700 |
| 5,610,202 A | | 3/1997 | Marchionna et al. ......... | 518/700 |
| 5,767,039 A | | 6/1998 | Yamagishi et al. ........... | 502/342 |
| 5,914,433 A | | 6/1999 | Marker ......................... | 585/313 |
| 6,049,017 A | | 4/2000 | Vora et al. ..................... | 585/324 |
| 6,054,497 A | | 4/2000 | Sofianos et al. .............. | 518/713 |
| 6,114,279 A | | 9/2000 | Fukui et al. ................... | 502/342 |

(Continued)

FOREIGN PATENT DOCUMENTS

| CA | 1207344 | 7/1986 |
|---|---|---|
| DE | 270296 | 7/1989 |

(Continued)

OTHER PUBLICATIONS

Arnold, C. Eng, E.; Fuglerud, E Vora; Kvisle, T., Nilsen, H.; "Integration of the UOP/HYDRO MTO Process into Ethylene Plants"; 10th Ethylene Producers' Conference, New Orleans, USA: 1998.

(Continued)

*Primary Examiner* — Taylor Victor Oh

(57) ABSTRACT

The present invention provides a process for producing ethylene oxide, comprising (a) cracking an ethane-comprising feed in a cracking zone under cracking conditions to obtain olefins including at least ethylene and hydrogen; (b) converting an oxygenate feedstock in an oxygenate-to-olefin zone to obtain olefins, including at least ethylene; providing at least part of the ethylene obtained in step (a) and /or (b) to an ethylene oxidation zone together with a feed containing oxygen and oxidizing ethylene to obtain at least ethylene oxide and carbon dioxide. At least part of the oxygenate feedstock is obtained by providing carbon dioxide obtained in step (c) and a feed containing hydrogen to an oxygenate synthesis zone and synthesizing oxygenates, which feed containing hydrogen comprises hydrogen obtained in step (a).

12 Claims, 1 Drawing Sheet

(56) References Cited

U.S. PATENT DOCUMENTS

| | | |
|---|---|---|
| 6,488,839 B1 | 12/2002 | Lenglet et al. |
| 6,677,496 B2 | 1/2004 | Netzer ............... 585/648 |
| 6,809,227 B2 | 10/2004 | Vaughn ............... 585/640 |
| 2002/0143220 A1 | 10/2002 | Griffiths et al. ......... 585/324 |
| 2004/0102667 A1 | 5/2004 | Vora et al. ............ 585/324 |
| 2004/0224841 A1 | 11/2004 | Matusz et al. ......... 502/347 |
| 2004/0225138 A1 | 11/2004 | McAllister et al. ..... 549/523 |
| 2005/0038304 A1 | 2/2005 | Van Egmond et al. ... 585/324 |
| 2007/0049647 A1 | 3/2007 | Van Egmond et al. |
| 2007/0129588 A1 | 6/2007 | Kalnes et al. |
| 2007/0155999 A1 | 7/2007 | Pujado et al. ......... 585/327 |
| 2007/0203380 A1 | 8/2007 | Vora et al. ............ 585/638 |
| 2008/0139853 A1 | 6/2008 | Boele et al. ........... 568/867 |
| 2008/0182999 A1 | 7/2008 | Rekers et al. ......... 549/512 |
| 2009/0234144 A1 | 9/2009 | Bos et al. ............. 549/534 |
| 2010/0206771 A1 | 8/2010 | Rothaemel et al. |

FOREIGN PATENT DOCUMENTS

| | | |
|---|---|---|
| DE | 10043644 | 3/2002 |
| EP | 0340576 | 11/1989 |
| WO | WO9515934 | 6/1995 |
| WO | WO0236532 | 5/2002 |
| WO | WO2006020083 | 2/2006 |
| WO | WO2007135052 | 11/2007 |
| WO | WO2007142739 | 12/2007 |
| WO | WO2008039552 | 4/2008 |
| WO | WO2009039948 | 4/2009 |
| WO | WO2009065848 | 5/2009 |
| WO | WO2009065855 | 5/2009 |
| WO | WO2009065870 | 5/2009 |
| WO | WO2009065875 | 5/2009 |
| WO | WO2009065877 | 5/2009 |

OTHER PUBLICATIONS

Weissermel, Klaus and Arpe, Hans-Jürgen: "Industrial Organic Chemistry"; 3rd Edition, Wiley; 1997.

Derrien, Michael L.; "Selective Hydrogenation Applied to the Refining of Petrochemical Raw Materials Produced by Steam Cracking"; Institut Francais de Petrole; pp. 613-666, 1986.

Curtis N.; "UOP/HYDRO MTO Applications: Opportunities for the Methanol to Olefins Process"; Asian Olefins and Derivatives Conference; Singapore; Jun. 18-19, 1998.

* cited by examiner

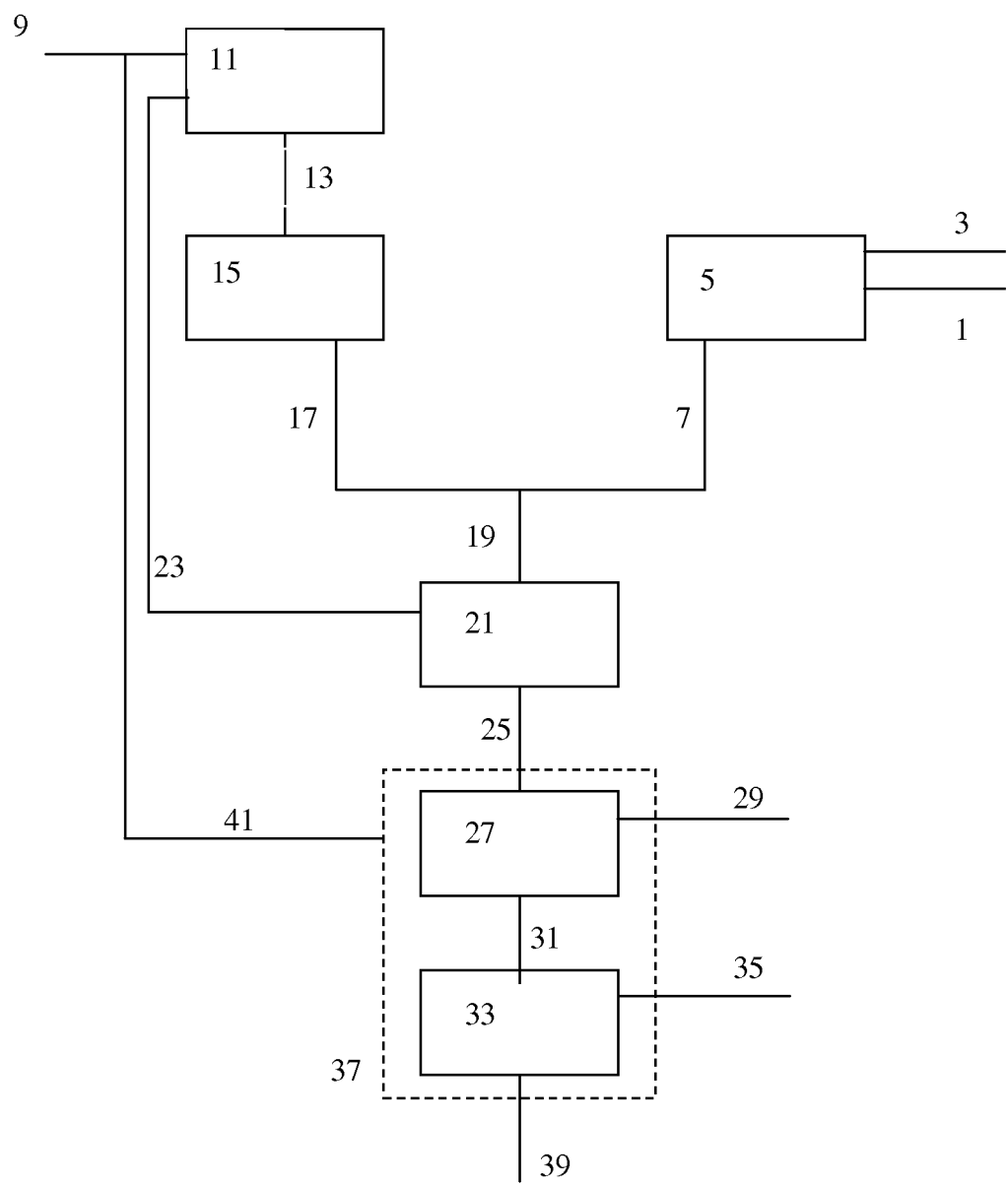

PROCESS FOR PRODUCING ETHYLENE OXIDE

This application claims the benefit of European Application No. 09175604.9 filed Nov. 10, 2009, which is incorporated herein by reference.

BACKGROUND

The invention relates to a process for producing ethylene oxide and an integrated system for producing ethylene oxide.

In recent years increasing attention is given to the exploration and utilisation of natural gas resources around the globe. A disadvantage of natural gas with respect to oil is the difficulty to transport large volumes of natural gas from the source to the market. One way of efficiently transporting natural gas is by liquefying the natural gas and to transport the liquefied natural gas (LNG). Another way is to convert the methane in the natural gas to liquid hydrocarbons using a Gas-to-Liquid process (GtL). The GtL products are typically liquid and can be transported in a similar way as traditional oil and oil products.

Besides methane, the natural gas typically comprises other hydrocarbons such as ethane, propane, and butanes. Such a natural gas is referred to as wet gas. The latter two can be added to the LPG pool, however, ethane cannot. Moreover, for various reasons the ethane content in the natural gas supplied to an LNG or GtL process is restricted and therefore a significant part of the ethane must be removed from the natural gas prior to providing the natural gas to either a LNG or GtL process.

Although, the application of ethane is limited, typically ethane is combusted in a furnace to provide heat; its corresponding olefin ethylene is a base chemical with a wide application and is of great commercial interest. Ethane can be converted into ethylene, e.g. using a thermal cracking process. Subsequently, the ethylene can be used to produce e.g. polyethylene, styrene or mono-ethylene-glycol. The conversion of ethane to ethylene is highly endothermic and requires significant energy input. In addition, the capex for the ethane to ethylene process, in particular the back-end work-up section, and the subsequent ethylene conversion processes is high and a minimum ethylene production capacity is required to make it economically benign.

When, the ethane content in the natural gas is too low, and consequently insufficient ethane is available, the ethane/ethylene route become unattractive.

This problem becomes even more pronounced, in case the natural gas is withdrawn from relatively small reservoirs, especially those located in remote, isolated locations, also referred to as stranded natural gas. Of course, this stranded natural gas may be converted to LNG or GtL products. However, this requires the stranded gas reservoir to sustain a minimum production level per day in order to make the investments worthwhile. Typically, such stranded natural gas reservoirs cannot achieve sufficient production levels to sustain a GtL or LNG plant. In addition, insufficient ethane is co-produced to sustain an ethane to ethylene process and subsequent ethylene conversion processes.

It has been suggested to combine an ethane steam cracker with an Oxygenate-to-Olefin (OTO) process, which can produce additional ethylene. For instance, C. Eng et al. (C. Eng, E. Arnold, E Vora, T. Fuglerud, S. Kvisle, H. Nilsen, Integration of the UOP/HYDRO MTO Process into Ethylene plants, 10$^{th}$ Ethylene Producers' Conference, New Orleans, USA, 1998) have suggested to combine UOP's Methanol-to-Olefins (MTO) process with a naphtha or ethane fed steam cracker. It is mentioned that by combining both processes sufficient ethylene can be produced, while coproducing valuable propylene. A disadvantage mentioned by C. Eng et al. is the fluctuating price of methanol, which is the primary feed to the MTO reaction.

In WO 2009/039948 A2, a combined stream cracking and OTO process is suggested for preparing ethylene and propylene. According to WO 2009/039948 A2, in this process, a particular advantage is obtained by combing the back-end of both processes. The methanol feedstock is produced from methane, requiring a sufficient supply of methane.

In US2005/0038304, an integrated system for producing ethylene and propylene from an OTO system and a steam cracking system is disclosed. According to US2005/0038304, in this process, a particular advantage is obtained by combining the back-end of both processes. The methanol feedstock to the OTO process is produced from synthesis gas. However, according to US2005/0038304 the production of methanol from synthesis gas has high energy requirements due to the endothermic nature of the synthesis gas production process. Such an endothermic synthesis gas production process is normally steam methane reforming.

As mentioned herein above, ethylene is a suitable intermediate to produce mono-ethylene-glycol. Monoethylene-glycol is a liquid at room temperature and can therefore be suitably transported. Mono-ethylene-glycol is produced by first oxidising ethylene to ethylene oxide. The disadvantage of converting the ethylene to mono-ethylene-glycol is that carbon dioxide is produced as a by-product of the ethylene oxidation process. This carbon dioxide has no further purpose and therefore must be sequestered or otherwise captured and stored in order reduce the carbon dioxide penalty of the process.

There is a need in the art for a process for preparing ethylene oxide and optionally mono-ethylene-glycol by an integrated ethane cracking and OTO process with a reduced carbon dioxide production.

SUMMARY OF THE INVENTION

It has now been found that it is possible to reduce the carbon dioxide production of such a process by using at least part of the carbon dioxide produced in preparation of ethylene oxide and optionally monoethylene-glycol to synthesise at least methanol and/or DME, which can be used as feedstock to the OTO process.

Accordingly, the present invention provides a process for producing ethylene oxide, comprising:
a) cracking an ethane-comprising feed in a cracking zone under cracking conditions to obtain olefins, including at least ethylene, and hydrogen;
b) converting an oxygenate feedstock in an oxygenate-to-olefin zone to obtain olefins, including at least ethylene;
c) providing at least part of the ethylene obtained in step (a) and/or (b) to an ethylene oxidation zone with a feed containing oxygen and oxidising ethylene to obtain at least ethylene oxide and carbon dioxide; and wherein at least part of the oxygenate feedstock is obtained by providing carbon dioxide obtained in step (c) and a feed containing hydrogen to an oxygenate synthesis zone and synthesising oxygenates, which feed containing hydrogen comprises hydrogen obtained in step (a).

BRIEF DESCRIPTION OF THE DRAWING

FIG. 1 is a schematic representation of an embodiment of an integrated system for producing ethylene oxide according to the invention.

DETAILED DESCRIPTION

The process according to the present invention is directed at producing ethylene oxide, and optionally mono-ethylene-glycol (MEG), lower olefins, in particular ethylene and propylene, and styrene. In the process the ethylene oxide is obtained by oxidising ethylene.

Several processes, such as ethane cracking or Oxygenate-to-Olefin (OTO) processes can produce ethylene. The ethane cracking and the OTO processes typically produce ethylene from different starting materials. In the case of the ethane cracking step, the feed is preferably an ethane-comprising feed. The OTO step on the other hand uses an oxygenate-comprising feed. Preferred oxygenates include alkylalcohols and alkylethers, more preferably methanol, ethanol, propanol and/or dimethylether (DME), even more preferably methanol and/or dimethylether (DME). In step (a) of the process, an ethane-comprising feed is provided to a cracking zone and cracked. The obtained cracking product comprises olefins and hydrogen.

In step (b) of the process an oxygenate feed is provided to an oxygenate-to-olefin zone and converted to obtain at least olefins.

In the process according to the invention at least part of obtained ethylene from the ethane cracking step (a) and/or the OTO step (b), preferably both steps (a) and (b) is oxidised to ethylene oxide by providing at least part of the ethylene with a feed containing oxygen to an ethylene oxidation zone, further referred to as EO zone.

Preferably, the ethylene oxide is further converted to mono-ethylene-glycol (MEG). MEG is a liquid and therefore can be transported and stored more conveniently than ethylene oxide. Preferably, the EO zone is part of a larger Mono-ethylene-glycol synthesis zone, i.e. a second oxygenate synthesis zone, further referred to as MEG zone. Preferably, the MEG zone then comprises a first section comprising the EO zone and a second ethylene oxide hydrolyses section. The MEG is synthesised by providing the ethylene oxide with a feed containing water to the ethylene oxide hydrolyse zone and converting the ethylene oxide to MEG. Optionally, the ethylene oxide is first reacted with carbon dioxide to from ethylene carbonate, which is subsequently hydrolysed to obtain MEG and carbon dioxide, reference herein is made to for instance US2008139853, incorporated by reference.

Ethylene is typically converted to ethylene oxide by oxidising ethylene to form ethylene oxide.

A by-product of the ethylene oxide process is carbon dioxide. During the reaction of ethylene with oxygen to ethylene oxide, carbon dioxide is formed as part of the ethylene is fully oxidised to carbon dioxide. The carbon dioxide is typically obtained as part of an EO zone effluent, which also comprises ethylene oxide. This is waste carbon dioxide and needs to be sequestered or otherwise captured and stored.

It has now been found that by producing ethylene oxide by an integrated process comprising an ethane cracking step and an Oxygenate-to-Olefin (OTO) step, a synergetic use of the feedstock is achieved by using at least part of the carbon dioxide that is produced by the ethylene oxide step (c) (further also referred to as carbon dioxide obtained from step (c) or carbon dioxide ex. EO) for synthesising oxygenates. These oxygenates are subsequently fed to the OTO reaction to form further olefins. By using carbon dioxide ex. EO, the carbon dioxide penalty for producing oxygenates is reduced as at least part of the carbon required for producing the oxygenate is obtained from waste carbon dioxide.

By providing part of the carbon dioxide ex. EO to the oxygenate synthesis zone the amount of synthesis gas needed to synthesise the oxygenates may be reduced. The synthesis gas is typically produced by partial oxidation of hydrocarbons using essentially pure oxygen or at least oxygen enriched air. The production of pure oxygen is highly energy consuming, therefore a reduction in the synthesis gas demand also reduces the oxygen demand, which in return results in decreased energy consumption and carbon dioxide production. Moreover, the capital investment can be reduced as a smaller oxygen production unit is required.

A further synergy is obtained by using at least part of the hydrogen produced by cracking the ethane-comprising in step (a) for synthesising oxygenates. By providing part of the hydrogen produced by cracking the ethane-comprising in step (a) to the oxygenate synthesis zone more carbon dioxide ex EO may be added and thus more carbon dioxide ex. EO may be captured in the form of methanol, ethylene and other products produced by the process according to the invention.

In the process according to the present invention at least part of the carbon dioxide ex. EO is provided to the oxygenate synthesis zone. Preferably, the carbon dioxide is separated from the EO zone effluent to obtain a separate carbon dioxide comprising stream. Preferably, the EO zone effluent is further treated to convert the ethylene oxide into MEG in a MEG zone. From the MEG zone a MEG zone effluent is obtained, comprising MEG and carbon dioxide. Suitably, the carbon dioxide can be separated from the MEG zone effluent by cooling the MEG zone effluent to a temperature below the boiling point of MEG, this carbon dioxide is also referred to as carbon dioxide ex. MEG. As no additional carbon dioxide is produced by converting ethylene oxide into MEG the carbon dioxide ex. MEG is the same as the carbon dioxide ex. EO. By reusing the carbon dioxide to synthesize oxygenates, the carbon dioxide penalty for producing EO is reduced. A further advantage is that the stream comprising carbon dioxide obtained from the EO or MEG zone comprises predominantly carbon dioxide and, depending on the temperature of the stream, steam. Preferably the stream comprises in the range of 80 to 100 mol % of carbon dioxide and steam, based on the total amount of moles in the stream. More preferably, the stream comprising carbon dioxide comprises essentially only carbon dioxide and, optionally, steam. Such a stream is particularly suitable to be used in a oxygenate synthesis process as it does not introduce significant amounts of inert, e.g. $CH_4$, $N_2$ and Ar, to the oxygenate synthesis zone. Should, however, the stream comprising carbon dioxide comprise significant amounts of other, undesired, compounds, e.g. ethylene oxide, the stream is preferably treated to remove such compounds prior to being introduced into the oxygenate synthesis zone. Typically, small amounts of chlorinated compounds are present during the oxidation of ethylene to EO. As a result the stream comprising carbon dioxide obtained from the EO or MEG zone may comprise alkylchlorides. The alkylchlorides content of the stream comprising carbon dioxide obtained from the EO or MEG zone can be determined using known analysis methods for determining the composition of a gas stream, such as gas chromatography. In case the stream comprising carbon dioxide obtained from the EO or MEG zone comprises alkylchlorides, the stream comprising carbon dioxide obtained from the EO or MEG zone preferably is first treated to remove alkylchlorides. The chlorine may be removed using any suitable method for removing chlorine from a gas stream. One such method includes stripping or extracting the alkylchlorides in an extraction unit. Another suitable process includes the removal of the alkylchlorides by a membrane.

Another advantage of the integration with a MEG synthesis is that next to MEG, minor amounts of other oxygenates may produced in the MEG zone by the process for producing MEG, such as for instance di-ethylene-glycol. These oxygenates may suitably be separated from the obtained MEG zone effluent and provided to the OTO zone as part of the oxygenate feed.

A synergy is achieved in the process according to the invention by using carbon dioxide ex. EO to produce at least part of the oxygenate feed to the OTO zone. As a result, the carbon dioxide ex. EO is no longer dissipated into the atmosphere or captured and stored, but rather used to produce valuable oxygenates. In addition, the carbon dioxide ex. EO does not comprise significant amounts of inerts such as $N_2$, Ar or $CH_4$. These inerts may typically be present in the natural gas or purified oxygen provided to produce synthesis gas for methanol production. By providing carbon dioxide ex. EO as part of the feed to the oxygenate synthesis zone the inert content in this feed may be reduced.

Further synergy is achieved as the process according to the invention allows the use of mixed feedstocks, e.g. a primarily methane/ethane feedstock, to produce ethylene oxide. In such a case the feedstock is split into a stream comprising predominantly ethane, which is cracked to ethylene, and a stream comprising predominantly methane, which is converted to synthesis gas and subsequently methanol and/or DME. The methanol and/or DME can be converted to ethylene using an OTO process. As a result the ethylene and MEG production is less vulnerable to variation in the feed supply of either methane or ethane.

As mentioned herein above, carbon dioxide ex. EO is used to produce at least part of the oxygenate feedstock provided to the OTO zone in step (b). Any suitable oxygenate or mixture of oxygenates may be produced, in particular alkylalcohols and alkylethers, preferably methanol and/or DME.

In the process according to the invention, carbon dioxide ex. EO and a feed containing hydrogen are provided to the oxygenate synthesis zone.

Methanol may be produced directly from hydrogen and carbon dioxide in the oxygenate synthesis zone. Hydrogen can react with carbon dioxide to produce methanol following:

$$CO_2 + 3H_2 \rightarrow CH_3OH + H_2O.$$

Preferably, the feed containing hydrogen also comprises carbon monoxide. The hydrogen may than also react with carbon monoxide to also form methanol following:

$$CO + 2H_2 \rightarrow CH_3OH.$$

Preferably, the carbon dioxide, hydrogen and preferably carbon monoxide are provided to the oxygenate synthesis zone in a molar ratio of in the range of from 2.0 to 3.0, preferably 2.0 to 2.2. The molar ratio herein is defined as:

$$\text{molar ratio} = (\#mol\ H_2 - \#mol\ CO_2)/(\#mol\ CO + \#mol\ CO_2).$$

In case a carbon monoxide is present to convert the hydrogen to methanol, it is preferred that the carbon dioxide concentration in the hydrogen, carbon monoxide and carbon dioxide mixture is in the range of from 0.1 to 25 mol %, preferably 3 to 15 mol %, more preferably of from 4 to 10 mol %, based on the total number of moles hydrogen, carbon monoxide and carbon dioxide in the mixture. The carbon dioxide content, relative to that of CO, in the syngas should be high enough so as to maintain an appropriately high reaction temperature and to minimize the amount of undesirable by-products such as paraffins. At the same time, the relative carbon dioxide to carbon monoxide content should not be too high so that the reaction of carbon dioxide with hydrogen yields less methanol based on the hydrogen provided to the oxygenate synthesis zone. In addition, the reaction of carbon dioxide with hydrogen yields water. If present in too high a concentration, water may deactivate the oxygenate synthesis catalyst.

In the oxygenate synthesis zone the hydrogen, carbon dioxide and preferably carbon monoxide are converted to methanol in the presence of a suitable catalyst. Such catalysts are known in the art and are for instance described in WO 2006/020083, which is incorporated herein by reference. Suitable catalysts for the synthesis of methanol from hydrogen, carbon dioxide and preferably carbon monoxide include:

An oxide of at least one element selected from the group consisting of copper, silver, zinc, boron, magnesium, aluminium, vanadium, chromium, manganese, gallium, palladium, osmium and zirconium.

Preferably, the catalyst is a copper and zinc based catalyst, more preferably in the form of copper, copper oxide, and zinc oxide.

A copper based catalyst, which includes an oxide of at least one element selected from the group consisting of silver, zinc, boron, magnesium, aluminium, vanadium, chromium, manganese, gallium, palladium, osmium and zirconium.

Preferably, the catalyst contains copper oxide and an oxide of at least one element selected from the group consisting of zinc, magnesium, aluminium, chromium, and zirconium.

A catalyst selected from the group consisting of: copper oxides, zinc oxides and aluminium oxides. More preferably, the catalyst contains oxides of copper and zinc.

A catalyst comprising copper oxide, zinc oxide, and at least one other oxide.

Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

Particular suitable catalysts include catalysts comprising in the range of from 10 to 70 wt % copper oxide, based on total weight of the catalyst. Preferably, comprising in the range of from 15 to 68 wt % copper oxide, and more preferably of from 20 to 65 wt % copper oxide, based on total weight of the catalyst.

Such catalyst may preferably also contain in the range of from 3 to 30 wt % zinc oxide, based on total weight of the catalyst. Preferably, it contains in the range of from 4 to 27 wt % zinc oxide, more preferably of from 5 to 24 wt % zinc oxide, based on total weight of the catalyst.

Catalysts comprising both copper oxide and zinc oxide, preferably comprise copper oxide and zinc oxide in a ratio of copper oxide to zinc oxide which may vary over a wide range. Preferably, such catalysts comprise copper oxide to zinc oxide in a Cu:Zn atomic ratio in the range of from 0.5:1 to 20:1, preferably of from 0.7:1 to 15:1, more preferably of from 0.8:1 to 5:1.

The catalyst can be prepared according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

Methanol may be synthesised in the oxygenate synthesis zone by any conventional methanol synthesis process. Examples of such processes include batch processes and continuous processes. Continuous processes are preferred. Tubular bed processes and fluidized bed processes are particularly preferred types of continuous processes.

The methanol synthesis process is effective over a wide range of temperatures. Preferably, methanol is synthesised in the oxygenate synthesis zone by contacting the hydrogen, carbon dioxide and preferably carbon monoxide with the catalyst at a temperature of in the range of from 150 to 450° C., more preferably of from 175 to 350° C., even more preferably of from 200 to 300° C.

The methanol synthesis process is effective over a wide range of pressures. Preferably, the methanol is synthesised by contacting the hydrogen, carbon dioxide and preferably carbon monoxide with the catalyst in the oxygenate synthesis zone at a pressure in the range of from 15 to 125 atmospheres, more preferably of from 20 to 100 atmospheres, more preferably of from 25 to 75 atmospheres.

For methanol synthesis, gas hourly space velocities in the oxygenate synthesis zone vary depending upon the type of continuous process that is used. Preferably, the gas hourly space velocity of flow of gas through the catalyst bed is in the range of from 50 $hr^{-1}$ to 50,000 $hr^{-1}$. Preferably, the gas hourly space velocity of flow of gas through the catalyst bed is in the range of from about 250 $hr^{-1}$ to 25,000 $hr^{-1}$, more preferably from about 500 $hr^{-1}$ to 10,000 $hr^{-1}$.

A methanol synthesis process as described herein above may produce several oxygenates as by-products, including aldehydes and other alcohols. Such by-products are also suitable reactants in the OTO reaction. Other less desirable by-products may be removed from the effluent of the oxygenate synthesis zone effluent if required prior to providing the oxygenate synthesis zone effluent to the OTO zone as to form at least part of the oxygenate feed.

Another suitable and preferred oxygenate, which may be synthesised in the oxygenate synthesis zone is dimethylether (DME). DME can be directly synthesized from hydrogen obtained in step (a) and at least one of carbon monoxide and carbon dioxide, but is preferably synthesized from methanol, which was at least in part produced from hydrogen obtained in step (a) as described herein above. Optionally, DME is obtained from methanol and hydrogen, carbon dioxide and preferably carbon monoxide. The conversion of methanol to DME is known in the art. This conversion is an equilibrium reaction. In the conversion the alcohol is contacted at elevated temperature with a catalyst. In EP-A 340 576 a list of potential catalysts are described. These catalysts include the chlorides of iron, copper, tin, manganese and aluminium, and the sulphates of copper, chromium and aluminium. Also oxides of titanium, aluminium or barium can be used. Preferred catalysts include aluminium oxides and aluminium silicates. Alumina is particularly preferred as catalyst, especially gamma-alumina. Although the methanol may be in the liquid phase the process is preferably carried out such that the methanol is in the vapour phase. In this context the reaction is suitably carried out at a temperature of 140 to 500° C., preferably 200 to 400° C., and a pressure of 1 to 50 bar, preferably from 8-12 bar, the exact choice depends on the acidity of the catalyst. In view of the exothermic nature of the conversion of methanol to DME the conversion is suitably carried out whilst the reaction mixture comprising the first catalyst is being cooled to maximize DME yield. Suitably, the methanol to DME reaction takes place in a separate section of the oxygenate synthesis zone.

In the case where part of the methanol synthesized is converted into DME, the effluent of the oxygenate zone may comprise methanol and DME in any ratio. Preferably, the ratio of DME to methanol weight ratio is in the range of from 0.5:1 to 100:1, more preferably from 2:1 to 20:1. Suitably the methanol to DME conversion reaction is led to equilibrium. This includes that the DME to methanol weight ratio may vary from 2:1 to 6:1. Evidently, the skilled person may decide to influence the equilibrium by applying different reaction conditions and/or by adding or withdrawing any of the reactants.

In the process according to the invention at least part of the oxygenate feed is methanol and/or DME produced by reacting carbon dioxide ex. EO with at least hydrogen.

The feed containing hydrogen may be any feed containing hydrogen available. A particularly suitable feed containing hydrogen is a feed comprising a synthesis gas obtained from a process for preparing synthesis gas. Such processes for preparing synthesis gas preferably include non-catalytic partial oxidation processes, catalytic partial oxidation processes, steam methane reforming processes, auto-thermal reforming processes, and water-gas-shift processes. Although a water-gas-shift process is in principle not a process for preparing a synthesis gas, the effluent of a water-gas-shift process typically comprises carbon monoxide, carbon dioxide and hydrogen. As can be seen in the definition of the molar ratio hereinabove, such a water-gas-shift does not influence the molar ratio obtained. The feed containing hydrogen may also comprise synthesis gas obtained from several processes for preparing synthesis gas.

Preferred feeds containing hydrogen are those that comprise synthesis gas having a hydrogen and carbon monoxide and/or carbon dioxide molar ratio, as defined herein above, which is above the ratio preferred for synthesising methanol, i.e. feeds containing hydrogen that are carbon deficient.

Preferably, a synthesis gas is used comprising little or no carbon dioxide. When using a synthesis gas with little or no carbon dioxide, more carbon dioxide ex. EO can be added and less inerts are introduced to the oxygenate synthesis zone, such low carbon dioxide comprising synthesis gases are therefore preferred, more preferred are synthesis gases comprising carbon dioxide in the range of from 0 to 8 mol % even more preferably of from 0.1 to 3 mol %, still even more preferably 0.2 to 2.5 mol %, based on the total number of moles in the synthesis gas.

Such low carbon dioxide synthesis gases are preferably produced by non catalytic partial oxidation processes for preparing synthesis gas. A partial oxidation catalyst typically induces some water-gas-shift in the presence of water. As a result carbon monoxide is shifted to carbon dioxide. An additional advantage is that non-catalytic partial oxidation processes do not require the addition of substantial amounts of water to the process. Processes producing substantial amounts of carbon dioxide include for instance Steam Methane Reforming. Therefore, the use of a synthesis gas from a Steam Methane Reforming process is less preferred.

The process according to the invention includes embodiments wherein the carbon dioxide ex. EO is provided to and/or mixed with an effluent of a syngas producing process and subsequently the at least part of the effluent, optionally after being processed in a water-gas-shift step, is used for the oxygenate synthesis process.

The use of a part of a synthesis gas stream, of which the remainder is used as a feed to a Fischer-Tropsch process, has the additional advantage that carbon dioxide in the synthesis gas stream can predominantly be directed towards the oxygenate synthesis process rather than to the Fischer-Tropsch process in which carbon dioxide is regarded as an undesired inert.

The feed containing hydrogen contains hydrogen produced by step (a) of the process according the invention. This hydrogen is obtained as co-product and does not add additional carbon dioxide on top what is required for the main reaction product ethylene.

A further suitable feed containing hydrogen is a feed comprising hydrogen produced by step (b) of the process according to the invention. This hydrogen is obtained as co-product and does not add additional carbon dioxide on top what is required for the main reaction product ethylene.

As mentioned herein above it is preferred to use both carbon dioxide and carbon monoxide to synthesise the oxygenates, while it is also preferred to combine the carbon dioxide ex. EO with a feed containing hydrogen that is rich in hydrogen, therefore preferably a synthesis gas is combined with at least hydrogen, for example obtained from step (a) of the process according to the invention to from the feed containing hydrogen. For example, a synthesis gas comprising mainly hydrogen and carbon monoxide at molar ratio of 1.6, may be combined with hydrogen, for example obtained from step (a) of the process according to the invention to form a feed containing hydrogen, which can be mixed with at least part of the carbon dioxide ex. EO. Preferably, sufficient carbon dioxide ex. EO is added to the synthesis gas to provide a carbon dioxide concentration in the range of from 0.1 to 25 mol %, preferably 3 to 15 mol %, more preferably of from 4 to 10 mol %, based on the total number of moles hydrogen, carbon monoxide and carbon dioxide in the mixture.

As mentioned, preferably, a synthesis gas is used comprising little or no carbon dioxide. The carbon dioxide ex. EO comprises little or no inerts like Ar, $N_2$ or $CH_4$. When using a synthesis gas with little or no carbon dioxide, more carbon dioxide ex. EO can be added and less inerts are introduced to the oxygenate synthesis zone. Less waste carbon dioxide is thus produced, which would otherwise need to be sequestrated or captured and stored.

In step (a) of the process, olefins, including ethylene, are produced. Typically the olefins, together with any other compounds leave the cracking zone as cracking zone effluent comprise olefins, including ethylene. Preferably, the ethylene is separated from the remainder of the cracking zone effluent, such as for instance hydrogen and propylene, prior to being provided to the MEG zone. The ethylene may be separated using any suitable means in the art. Reference is made to for instance US2005/0038304.

In step (b) of the process, olefins, including ethylene are also produced, which typically leave the OTO zone as part of an OTO zone effluent. As for the ethylene produced in step (a) it is preferred to separate the ethylene from the remainder of the OTO zone effluent prior to providing any of the ethylene to the EO zone.

It has been found advantageous to combine at least part of the cracking zone effluent and the OTO zone effluent to form a combined effluent prior to separating the ethylene. By separating the ethylene from the combined effluent, rather than from the separate effluents, efficient use can be made of the back-end facilities of the processes.

By combining the cracking zone effluent and the OTO zone effluent a further advantage is obtained. In step (a) of the process hydrogen is produced in significant amounts. However, in step (b) of the process also some hydrogen is produced. The OTO zone effluent may therefore also comprise small amounts of hydrogen, typically in the range of from 0.05 to 1 wt % based on the total hydrocarbon content in the OTO zone effluent. The amount of hydrogen in the OTO zone effluent, however, is relatively small, making separating of the hydrogen from the remainder of the OTO zone effluent not worthwhile. By combining at least part of the cracking zone effluent and at least part of the OTO zone effluent to a combined effluent and subsequently separating hydrogen from that combined effluent it is possible to retrieve not only part or all of the hydrogen in the cracking zone effluent, but also at least part of the hydrogen in the OTO zone effluent. The hydrogen may be separated using any suitable means known in the art, for example cryogenic distillation and pressure swing absorption whereby hydrogen in the hydrogen containing stream absorbs preferentially over the impurities or via hydrogen permeable membranes.

The hydrogen obtained from the combined effluent may suitably be used to form at least part of the feed containing hydrogen provided with the carbon dioxide ex. EO to the oxygenate synthesis zone. By combining the effluents of the cracking zone and the OTO zone, also the hydrogen in the OTO zone effluent is retrieved. Thereby, the amount of hydrogen available to add to the field carbon dioxide and synthesis gas provided to the oxygenate synthesis zone to synthesise oxygenates is increased. Consequently, more field carbon dioxide can be provided to the oxygenate synthesis zone and thus more carbon dioxide is captured in the form of methanol, ethylene and other products.

By combining at least part of the cracking zone effluent and at least part of the OTO zone effluent to form a combined effluent, at least part of the olefins obtained in step (a) and step (b) are also combined in one stream.

The cracker zone effluent obtained from the cracking zone of step (a) comprises predominantly ethylene, but may also comprise up to 2 wt % propylene, based on the total weight of the ethylene in the cracking zone effluent. This amount of propylene is not economically recoverable, however by combining the olefins obtained from the cracking zone in step (a) and the olefins obtained from the OTO zone in step (b), i.e. combining at least part of the cracking zone effluent and at least part of the OTO zone effluent to a combined effluent, a combined effluent is obtained that comprises in the range of 10 to 40% of propylene, based on the total hydrocarbon content in the combined effluent. The high propylene content in the combined effluent is caused by the high propylene content in the OTO zone effluent. OTO processes produce a mix of olefins, comprising in the range of from 5 to 80 wt % of ethylene and in the range of from 10 to 80 wt % of propylene, based on the total hydrocarbon content in the OTO zone effluent. By combining the effluent of the cracking zone and the OTO zone, it is possible to also economically recover the propylene in the cracking zone effluent. The propylene can be used as a feedstock to a polypropylene production process, optionally after being treated to remove impurities. Polypropylene production processes are well known in the art.

Besides olefins and hydrogen, the OTO process also produces small amounts of alkanes, in particular ethane, propane and butane. A further synergy of the integrated process can be obtained by providing any ethane present in the effluent of the OTO zone to the cracking zone. The ethane can then be cracked to ethylene and hydrogen in the cracking zone, thus providing additional ethylene and hydrogen. The hydrogen may subsequently be used to synthesise oxygenates.

Part of the ethylene produced in the process according to the invention can be used as a feedstock for several other processes other than the synthesis of EO, including the production of styrene monomer.

It has now also been found that it is possible to integrate the production of these products into the process according to the invention to obtain further synergy.

A further integration may be achieved by converting at least part of the ethylene produced in step (a), step (b) or, preferably, both steps (a) and (b) with benzene into ethyl benzene and converting at least part of the ethyl benzene to styrene monomer and at least hydrogen.

Each of the mentioned conversion steps herein above are well known in the art. Any suitable process may be used.

Ethyl benzene is typically produced by reacting ethylene and benzene in the presence of an acid catalyst. Reference is for example made to Kniel et al., Ethylene, Keystone to the petrochemical industry, Marcel Dekker, Inc, New York, 1980, in particular section 3.4.1, pages 24 to 25. While the styrene is produced by the catalytic dehydrogenation of ethyl benzene in the presence of a suitable catalyst, examples of suitable catalysts include but are not limited to dehydrogenation catalysts based on iron(III) oxide.

By integrating the process according to the invention with the production of styrene monomer, as described above, further hydrogen is produced next to the desired products. Preferably, this hydrogen is separated from the other reaction products, and subsequently provided to the oxygenate synthesis zone as part of the feed containing hydrogen to prepare at least part of the oxygenate feed to step (b) of the process.

By providing additional hydrogen obtained from the conversion of ethylene, via ethylbenzene, into styrene to synthesise oxygenates more carbon dioxide ex. EO can be provided to the oxygenate synthesis zone, thereby further decreasing the carbon dioxide penalty for producing ethylene oxide.

In addition, the amount of synthesis gas needed to synthesise the oxygenates may be reduced. The synthesis gas is typically produced by partial oxidation of hydrocarbons using essentially pure oxygen or at least oxygen enriched air. The production of pure oxygen is highly energy consuming, therefore a reduction in the synthesis demand also reduces the oxygen demand, which in return results in decreased energy consumption and carbon dioxide production. Moreover, the capital investment can be reduced as a smaller oxygen production unit is required.

The produced styrene monomer may be used to produce polystyrene.

Carbon dioxide from other sources than the ethylene oxide synthesis process may also be provided to the oxygenate synthesis zone, in particular in the case where the amount of carbon dioxide ex. EO is insufficient to satisfy the full carbon dioxide demand of the oxygenate synthesis. As mentioned herein above some additional carbon dioxide may for instance be comprised in synthesis gas provided to the oxygenate synthesis as part of the feed containing hydrogen. Other suitable sources of carbon dioxide may include:

- a source comprising carbon dioxide obtained from a sub-surface natural gas or oil reservoir. Such carbon dioxide is also referred to as field carbon dioxide. Some subsurface natural gas or oil reservoir comprise substantial concentrations of carbon dioxide, up to 70 mol % based on the total content of the gas extracted from the reservoir. By using this carbon dioxide to synthesise oxygenates and subsequently olefins, this carbon dioxide is captured, reducing the carbon dioxide penalty for exploiting the subsurface natural gas or oil reservoir.
- a source comprising carbon dioxide obtained from a carbon dioxide-comprising flue gas stream, in particular a flue gas obtained from the integrated process according to the invention or optionally an oxygen purification unit or synthesis gas production process. The oxidation of ethylene to ethylene oxide requires large amounts of purified oxygen. Preferably, the flue gas is first concentrated to increase the carbon dioxide concentration.
- a source comprising the flue gas obtained from an oxidative de-coking of an ethane cracking furnace, typically one of the ethane cracking furnaces used for producing olefins in step (a). In case the oxidative de-coking of the furnace is done using pure oxygen or pure oxygen diluted in carbon dioxide instead of air, an essentially pure stream of carbon dioxide can be produced, which is especially suitable to be used in the synthesis to oxygenates. Although, it is required to first produce pure oxygen, there is no need to post-treat the flue gas in order to capture the carbon dioxide. Also the decoking to the OTO catalyst during regeneration of the catalyst can be performed in a similar way to provide a suitable carbon dioxide comprising stream.

In one embodiment the invention includes:
i) providing a feed comprising methane and ethane;
ii) separating the feed into at least a methane-comprising feed and an ethane-comprising feed;
iii) providing at least part the methane-comprising feed to a process for preparing synthesis gas to obtain a synthesis gas; and
iv) providing at least part of the ethane to the cracking zone and at least part of the synthesis gas to the oxygenate synthesis zone.

Preferably, oxygenates are synthesised in the oxygenate synthesis zone by converting the carbon dioxide with hydrogen into at least methanol and/or dimethylether.

In this case the invention allows for the co-production of ethylene oxide, propylene and optionally ethylene from a feed comprising methane and ethane, such as for example a natural gas or associated gas. By converting at least part of the ethylene oxide with at least water to MEG, also MEG can be co-produced. Reference herein to associated gas is to C1 to C5 hydrocarbons co-produced with the production of oil. The second process according to the invention provides the same advantages as described herein above for the first process and can advantageously be combined with a process for producing MEG or a process for producing styrene monomer, as described herein above for the first process.

In the present invention an ethane-comprising feed is cracked in a cracking zone under cracking conditions to produce at least olefins and hydrogen.

Additionally, small amounts of propylene are formed. Other by-products may be formed such as butylene, butadiene, ethyne, propyne and benzene. The cracking process is performed at elevated temperatures, preferably in the range of from 650 to 1000° C., more preferably from 750 to 950° C. Typically, the cracking is performed in the presence of water (steam) as a diluent. The ethane conversion is typically in the range of from 40 to 75 mol %, based on the total number of moles of ethane provided to the cracking zone. Preferably, the un-cracked ethane is recycled back to the cracking zone. Ethane cracking processes are well known to the skilled person and need no further explanation. Reference is for instance made to Kniel et al., Ethylene, Keystone to the petrochemical industry, Marcel Dekker, Inc, New York, 1980, in particular chapters 6 and 7.

In the present invention an oxygenate feedstock is converted in an oxygenate-to-olefins process, in which an oxygenate feedstock is contacted in an OTO zone with an oxygenate conversion catalyst under oxygenate conversion conditions, to obtain a conversion effluent comprising lower olefins. In the OTO zone, at least part of the feed is converted into a product containing one or more olefins, preferably including light olefins, in particular ethylene and/or propylene.

Examples of oxygenates that can be used in the oxygenate feedstock of step b) of the process include alcohols, such as methanol, ethanol, isopropanol, ethylene glycol, propylene glycol; ketones, such as acetone and methylethylketone; aldehydes, such as formaldehyde, acetaldehyde and propionaldehyde; ethers, such as dimethylether, diethylether, methylethylether, tetrahydrofuran and dioxane; epoxides such as ethylene oxide and propylene oxide; and acids, such as acetic acid, propionic acid, formic acid and butyric acid. Further examples are dialkyl carbonates such as dimethyl carbonate or alkyl esters of carboxylic acids such as methyl formate. Of these examples, alcohols and ethers are preferred.

Examples of preferred oxygenates include alcohols, such as methanol, ethanol, isopropanol, ethylene glycol, propylene glycol; and dialkyl ethers, such as dimethylether, diethylether, methylethylether. Cyclic ethers such as tetrahydrofuran and dioxane, are also suitable.

The oxygenate used in the process according to the invention is preferably an oxygenate which comprises at least one oxygen-bonded alkyl group. The alkyl group preferably is a C1-C4 alkyl group, i.e. comprises 1 to 4 carbon atoms; more preferably the alkyl group comprises 1 or 2 carbon atoms and most preferably one carbon atom. The oxygenate can comprise one or more of such oxygen-bonded C1-C4 alkyl groups. Preferably, the oxygenate comprises one or two oxygen-bonded C1-C4 alkyl groups.

More preferably an oxygenate is used having at least one C1 or C2 alkyl group, still more preferably at least one C1 alkyl group.

Preferably the oxygenate is chosen from the group of alkanols and dialkyl ethers consisting of dimethylether, diethylether, methylethylether, methanol, ethanol, isopropanol, and mixtures thereof.

Most preferably the oxygenate is methanol or dimethylether, or a mixture thereof.

Preferably the oxygenate feedstock comprises at least 50 wt % of oxygenate, in particular methanol and/or dimethylether, based on total hydrocarbons, more preferably at least 80 wt %, most preferably at least 90 wt %.

The oxygenate feedstock can be obtained from a prereactor, which converts methanol at least partially into dimethylether. In this way, water may be removed by distillation and so less water is present in the process of converting oxygenate to olefins, which has advantages for the process design and lowers the severity of hydrothermal conditions the catalyst is exposed to.

The oxygenate feedstock can comprise an amount of diluents, such as water or steam.

A variety of OTO processes are known for converting oxygenates such as for instance methanol or dimethylether to an olefin-containing product, as already referred to above. One such process is described in WO-A 2006/020083, incorporated herein by reference, in particular in paragraphs [0116]-[0135]. Processes integrating the production of oxygenates from synthesis gas and their conversion to light olefins are described in US2007/0203380A1 and US2007/0155999A1.

Catalysts as described in WO A 2006/020083 are suitable for converting the oxygenate feedstock in step (b) of the present invention. Such catalysts preferably include molecular sieve catalyst compositions. Suitable molecular sieves are silicoaluminophosphates (SAPO), such as SAPO-17, -18, -34, -35, -44, but also SAPO-5, -8, -11, -20, -31, -36, -37, -40, -41, -42, -47 and -56.

Alternatively, the conversion of the oxygenate feedstock may be accomplished by the use of an aluminosilicate catalyst, in particular a zeolite. Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Aluminosilicate catalysts are preferred when an olefinic co-feed is fed to the oxygenate conversion zone together with oxygenate, for increased production of ethylene and propylene.

The reaction conditions of the oxygenate conversion include those that are mentioned in WO-A 2006/020083. Hence, a reaction temperature of 200 to 1000° C., preferably from 250 to 750° C., and a pressure from 0.1 kPa (1 mbar) to 5 MPa (50 bar), preferably from 100 kPa (1 bar) to 1.5 MPa (15 bar), are suitable reaction conditions.

A specially preferred OTO process for use in step (b) of the present invention will now be described. This process provides particularly high conversion of oxygenate feed and a recycle co-feed to ethylene and propylene. Reference is made in this regard also to WO2007/135052, WO2009/065848, WO2009/065875, WO2009/065870, WO2009/065855, WO2009/065877, in which processes a catalyst comprising an aluminosilicate or zeolite having one-dimensional 10-membered ring channels, and an olefinic co-feed and/or recycle feed is employed.

In this process, the oxygenate-conversion catalyst comprises one or more zeolites having one-dimensional 10-membered ring channels, which are not intersected by other channels, preferably at least 50% wt of such zeolites based on total zeolites in the catalyst. Preferred examples are zeolites of the MTT and/or TON type. In a particularly preferred embodiment the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11. Such further zeolite (molecular sieve) can have a beneficial effect on the stability of the catalyst in the course of the OTO process and under hydrothermal conditions. The second molecular sieve having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80, more preferably at least 100, even more preferably at least 150. The oxygenate conversion catalyst can comprise at least 1 wt %, based on total molecular sieve in the oxygenate conversion catalyst, of the second molecular sieve having more-dimensional channels, preferably at least 5 wt %, more preferably at least 8 wt %, and furthermore can comprise less than 35 wt % of the further molecular sieve, in certain embodiments less than 20 wt %, or less than 18 wt %, such as less than 15 wt %.

Especially when the oxygenate conversion is carried out over a catalyst containing MTT or TON type aluminosilicates, it may be advantageous to add an olefin-containing co-feed together with the oxygenate feed (such as dimethylether-rich or methanol-rich) feed to the OTO zone when the latter feed is introduced into this zone. It has been found that the catalytic conversion of the oxygenates, in particular methanol and DME, to ethylene and propylene is enhanced when an olefin is present in the contact between methanol and/or dimethylether and the catalyst. Therefore, suitably, an olefinic co-feed is added to the reaction zone together with the oxygenate feedstock.

In special embodiments, at least 70 wt % of the olefinic co-feed, during normal operation, is formed by a recycle stream of a C3+ or C4+ olefinic fraction from the OTO conversion effluent, preferably at least 90 wt %, more preferably at least 99 wt %, and most preferably the olefinic co-feed is during normal operation formed by such recycle stream. In one embodiment the olefinic co-feed can comprise at least 50 wt % of C4 olefins, and at least a total of 70 wt % of C4 hydrocarbon species. It can also comprise propylene. The OTO conversion effluent can comprise 10 wt % or less, preferably 5 wt % or less, more preferably 1 wt % or less, of C6-C8 aromatics, based on total hydrocarbons in the effluent. At least one of the olefinic co-feed, and the recycle stream, can in particular comprise less than 20 wt % of C5+ olefins, preferably less than 10 wt % of C5+ olefins, based on total hydrocarbons in the olefinic co-feed.

In order to maximize production of ethylene and propylene, it is desirable to maximize the recycle of C4 olefins. In a stand-alone process, i.e. without integration with a cracker, there is a limit to the maximum recycle of a C4 fraction from the OTO effluent. A certain part thereof, such as between 1 and 5 wt %, needs to be withdrawn as purge, since otherwise saturated C4's (butane) would build up which are substantially not converted under the OTO reaction conditions.

In the preferred process, optimum light olefins yield are obtained when the OTO conversion is conducted at a temperature of more than 450° C., preferably at a temperature of 460° C. or higher, more preferably at a temperature of 480° C. or higher, in particular at 500° C. or higher, more in particular 550° C. or higher, or 570° C. or higher. The temperature will typically less than 700° C., or less than 650° C. The pressure will typically be between 0.5 and 15 bar, in particular between 1 and 5 bar.

In a special embodiment, the oxygenate conversion catalyst comprises more than 50 wt %, preferably at least 65 wt %, based on total molecular sieve in the oxygenate conversion catalyst, of the one-dimensional molecular sieve having 10-membered ring channels.

In one embodiment, molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 500° C. for 1 hour or more. The molecular sieves obtained after ion-exchange are also referred to as being in the ammonium form.

The molecular sieve can be used as such or in a formulation, such as in a mixture or combination with a so-called binder material and/or a filler material, and optionally also with an active matrix component. Other components can also be present in the formulation. If one or more molecular sieves are used as such, in particular when no binder, filler, or active matrix material is used, the molecular sieve itself is/are referred to as oxygenate conversion catalyst. In a formulation, the molecular sieve in combination with the other components of the mixture such as binder and/or filler material is/are referred to as oxygenate conversion catalyst.

It is desirable to provide a catalyst having good mechanical or crush strength, because in an industrial environment the catalyst is often subjected to rough handling, which tends to break down the catalyst into powder-like material. The latter causes problems in the processing. Preferably the molecular sieve is therefore incorporated in a binder material. Examples of suitable materials in a formulation include active and inactive materials and synthetic or naturally occurring zeolites as well as inorganic materials such as clays, silica, alumina, silica-alumina, titania, zirconia and aluminosilicate. For present purposes, inactive materials of a low acidity, such as silica, are preferred because they may prevent unwanted side reactions which may take place in case a more acidic material, such as alumina or silica-alumina is used.

Typically the oxygenate conversion catalyst deactivates in the course of the process. Conventional catalyst regeneration techniques can be employed. The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent oxygenate conversion catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 μm, preferably 50-100 μm.

The preferred embodiment of step (b) described hereinabove is preferably performed in an OTO zone comprising a fluidized bed or moving bed, e.g. a fast fluidized bed or a riser reactor system, although in general for an OTO process, in particular for an MTP process, also a fixed bed reactor or a tubular reactor can be used. Serial reactor systems can be employed. In one embodiment, the OTO zone comprises a plurality of sequential reaction sections. Oxygenate can be added to at least two of the sequential reaction sections.

When multiple reaction zones are employed, an olefinic co-feed is advantageously added to the part of the dimethyl-ether-rich feed that is passed to the first reaction zone.

The preferred molar ratio of oxygenate in the oxygenate feedstock to olefin in the olefinic co-feed provided to the OTO conversion zone depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5 and still more preferably in the range of 15:1 to 1:3.

A diluent can also be fed to the OTO zone, mixed with the oxygenate and/or co-feed if present, or separately. A preferred diluent is steam, although other inert diluents can be used as well. In one embodiment, the molar ratio of oxygenate to diluent is between 10:1 and 1:10, preferably between 4:1 and 1:2, most preferably between 3:1 and 1:1, such as or 1.5:1, in particular when the oxygenate is methanol and the diluent is water (steam).

The conversion of ethylene to ethylene oxide may be done by any ethylene oxidation process that produces at least ethylene oxide and carbon dioxide. In the EO zone, at least a part of the ethylene is partly oxidised to form ethylene oxide. Preferably, the oxidation of ethylene takes place in the EO zone to which the ethylene and a feed containing oxygen are provided. Preferably, the feed containing oxygen is oxygen-enriched air or, more preferably pure oxygen. The oxidation of ethylene may be performed over a catalyst present in the first section, preferably a silver based catalyst. Reference is for example made to made to Kniel et al., Ethylene, Keystone to the petrochemical industry, Marcel Dekker, Inc, New York, 1980, in particular page 20. As a by-product of the oxidation of ethylene to ethylene oxide, carbon dioxide is formed. Without wishing to be bound to any theory, the production of carbon dioxide is believed to originate from a reaction of ethylene with catalyst bound oxygen atoms. As a consequence in the range of from 14 to 20 mol % of the total amount of ethylene provided to the EO zone is converted into carbon dioxide.

The conversion of ethylene oxide to MEG may be done using any MEG producing process that uses ethylene oxide. Typically the ethylene oxide is hydrolysed with water to MEG. Optionally, the ethylene oxide is first converted with carbon dioxide to ethylene carbonate, which is subsequently hydrolysed to MEG and carbon dioxide. The water is provided to the MEG zone as a feed containing water, preferably pure water or steam. The MEG product is obtained from the MEG zone as a MEG-comprising effluent. Suitable processes for the production of ethylene oxide and MEG are described for instance in US2008139853, US2009234144, US2004225138, US2004224841 and US2008182999, herein incorporated by reference, however any suitable process for producing ethylene oxide and converting the ethylene oxide to MEG may be used.

The ethane-comprising feed to step (a) of the first process for producing olefins according to the invention may be any ethane-comprising feed. Prior to entering the cracking zone the ethane-comprising feed may be combined with one or more recycled process streams originating from either the cracking zone, OTO zone, or any other origin in the process. Besides ethane, the ethane-comprising feed may also comprise higher paraffins such as propanes and butanes. Preferably, the ethane-comprising feed comprises in the range of from 50 to 100 mol % of ethane, more preferably 80 to 99 mol % of ethane, based on the total number of moles in the ethane-comprising feed.

Preferably, the ethane-comprising feed is obtained from natural gas or associated gas.

The oxygenate feedstock provided to step (b) of the first process for producing olefins according to the invention may be any oxygenate-comprising feedstock. The oxygenate feedstock comprises at least methanol and/or DME obtained by providing hydrogen ex. cracker and a feed containing carbon monoxide and/or carbon dioxide to an oxygenate synthesis zone and converting hydrogen with carbon monoxide and/or carbon dioxide into methanol and/or dimethylether. The oxygenate feedstock may further comprise oxygenates, such as for example other alcohols, other ethers, aldehydes, ketones and esters. Preferably, the oxygenate feedstock comprises water as a diluent. The oxygenate feedstock may also comprise compounds other than water and oxygenates.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

Preferably, at least part of the oxygenate feed is obtained by converting methane into synthesis gas and providing the synthesis gas to a oxygenate synthesis zone to synthesise oxygenates. The methane is preferably obtained from natural gas or associated gas, more preferably the same natural gas or associated gas, from which the light paraffin feedstock for the cracker is obtained.

The oxygenate feedstock may be provided directly from one or more oxygenate synthesis zones, however, it may also be provided from a central oxygenate storage facility.

The olefinic co-feed optionally provided together with the oxygenate feedstock to the OTO zone may contain one olefin or a mixture of olefins. Apart from olefins, the olefinic co-feed may contain other hydrocarbon compounds, such as for example paraffinic, alkylaromatic, aromatic compounds or a mixture thereof. Preferably the olefinic co-feed comprises an olefinic fraction of more than 50 wt %, more preferably more than 60 wt %, still more preferably more than 70 wt %, which olefinic fraction consists of olefin(s). The olefinic co-feed can consist essentially of olefin(s).

Any non-olefinic compounds in the olefinic co-feed are preferably paraffinic compounds. If the olefinic co-feed contains any non-olefinic hydrocarbon, these are preferably paraffinic compounds. Such paraffinic compounds are preferably present in an amount in the range from 0 to 50 wt %, more preferably in the range from 0 to 40 wt %, still more preferably in the range from 0 to 30 wt %.

By an olefin is understood an organic compound containing at least two carbon atoms connected by a double bond. A wide range of olefins can be used. The olefin can be a mono-olefin, having one double bond, or a poly-olefin, having two or more double bonds. Preferably olefins present in the olefinic co-feed are mono-olefins.

The olefin(s) can be a linear, branched or cyclic olefin. Preferably olefins present in the olefinic co-feed are linear or branched olefins.

Preferred olefins have in the range from 2 to 12, preferably in the range from 3 to 10, and more preferably in the range from 4 to 8 carbon atoms.

Examples of suitable olefins that may be contained in the olefinic co-feed include ethene, propene, butene (one or more of 1-butene, 2-butene, and/or iso-butene (2-methyl-1-propene)), pentene (one or more of 1-pentene, 2-pentene, 2-methyl-1-butene, 2-methyl-2-butene, 3-methyl-1-butene, and/or cyclopentene), hexene (one or more of 1-hexene, 2-hexene, 3-hexene, 2-methyl-1-pentene, 2-methyl-2-pentene, 3-methyl-1-pentene, 3-methyl-2-pentene, 4-methyl-1-pentene, 4-methyl-2-pentene, 2,3-dimethyl-1-butene, 2,3-dimethyl-2-butene, 3,3-dimethyl-1-butene, methylcyclopentene and/or cyclohexene), heptenes, octenes, nonenes and decenes. The preference for specific olefins in the olefinic co-feed may depend on the purpose of the process.

In a preferred embodiment the olefinic co-feed preferably contains olefins having 4 or more carbon atoms (i.e. $C_4+$ olefins), such as butenes, pentenes, hexenes and heptenes. More preferably the olefinic fraction of the olefinic co-feed comprises at least 50 wt % of butenes and/or pentenes, even more preferably at least 50% wt of butenes, and most preferably at least 90 wt % of butenes. The butene may be 1-, 2-, or iso-butene. Most conveniently it is a mixture thereof.

Preferably, at least part of the oxygenate feed is obtained by converting methane into synthesis gas and providing the synthesis gas to a oxygenate synthesis zone to synthesise oxygenates. The methane is preferably obtained from natural gas or associated gas, more preferably the same natural gas or associated gas, from which the ethane-comprising feed was obtained.

The benzene used to convert ethylene into ethyl benzene may be any benzene available. The benzene may be benzene produced in step (a) of the process according to the invention. As disclosed in U.S. Pat. No. 6,677,496, ethane cracking processes typically produce up to 0.6 wt % of benzene, based on the total ethane feed. However, the benzene may also be obtained from any other source. Preferably, the benzene is produced from higher hydrocarbons such as propane and butane, more preferably propane and butane obtained as condensate or LPG from natural gas or associated gas, even more preferably the same natural gas or associated gas, from which the ethane-comprising feed was obtained.

The feed to the second process for producing olefins according to the invention may be any feed comprising methane and ethane. Preferably, the feed comprising methane and ethane is natural gas or associated gas.

Preferably, the feed comprising methane and ethane comprises in the range of from 1 to 20 mol % of ethane, based on the total feed.

In a further aspect, the invention provides an integrated system for producing ethylene oxide, which system comprises:

a) a steam cracking system having one or more inlets for an ethane-comprising feedstock and steam, and an outlet for a cracker effluent comprising olefins, including at least ethylene, and hydrogen;

b) an oxygenate-to-olefins conversion system, having one or more inlets for receiving an oxygenate feedstock, and comprising a reaction zone for contacting the oxygenate feedstock with an oxygenate conversion catalyst under oxygenate conversion conditions, and an outlet for a oxygenate-to-olefins effluent comprising olefins, including at least ethylene;

c) a work-up system arranged to receive at least part of the cracker effluent and at least part of the oxygenate-to-olefins effluent to obtain a combined effluent, the work-up section comprising a separation system, an outlet for ethylene and an outlet for hydrogen;

d) an ethylene oxidation system, having at least an inlet for ethylene and an inlet for oxygen and an outlet for ethylene oxide and an outlet for carbon dioxide, and comprising an ethylene oxidation zone for oxidising ethylene to ethylene oxide and carbon dioxide;

e) an oxygenate synthesis system having one or more inlets for a feed containing hydrogen and an inlet for carbon dioxide, and an outlet for an oxygenate feedstock; and means for providing carbon dioxide from the outlet for carbon dioxide of the ethylene oxidation system to the carbon dioxide inlet of the oxygenate synthesis system and means for providing hydrogen from the outlet for hydrogen of the work-up section to the inlet for a feed containing hydrogen of the oxygenate synthesis system. Optionally, the carbon dioxide ex. EO is mixed with the feed containing hydrogen prior to entering the oxygenate synthesis system. In that case, the inlets for feed containing hydrogen and the inlet for carbon dioxide of the oxygenate synthesis system may be the same inlet.

Preferably, the ethylene oxidation system forms part of a larger MEG synthesis system, together with a ethylene oxide hydrolysis system. In that case, the outlet for carbon dioxide of the ethylene oxidation system may be the outlet for carbon dioxide of the MEG synthesis system. The ethylene oxide hydrolysis system, preferably comprises an inlet for ethylene oxide, an inlet for water and an outlet for MEG, further comprising an ethylene oxide hydrolysis zone for hydrolysing ethylene oxide to MEG.

In an even further aspect, the invention provides a use of hydrogen obtained from a process to crack ethane to ethylene to produce an oxygenate feed for an oxygenate-to-olefin process.

In FIG. 1, a schematic representation is given of an embodiment of integrated system for producing ethylene oxide according to the invention. In the system of FIG. 1, a ethane-comprising feed and steam are provided via conduits 1 and 3 respectively to steam cracking system 5, comprising a cracking zone for steam cracking ethane to ethylene. From steam cracking system 5, a cracking zone effluent is retrieved via conduit 7.

In FIG. 1, also a feed containing carbon monoxide and/or carbon dioxide, e.g. a synthesis gas is provided via conduit 9 to oxygenate synthesis system 11, comprising an oxygenate synthesis zone for synthesizing oxygenates from hydrogen, carbon dioxide and carbon monoxide. From oxygenate synthesis system 11, an oxygenate feedstock is retrieved via conduit 13. The oxygenate feedstock is provided to oxygenate-to-olefins conversion system 15, comprising an OTO zone for converting oxygenates to lower olefins, e.g. ethylene and propylene. Optionally, an olefinic co-feed (not shown) is provided to oxygenate-to-olefins conversion system 15 together with the oxygenate feedstock. From oxygenate-to-olefins conversion system 13, an OTO zone effluent is retrieved via conduit 17.

The cracking zone effluent and the OTO zone effluent are combined to form a combined effluent in conduit 19 and provided to work-up section 21. Work-up section 21 comprises at least a separation system to separate ethylene from the combined effluent. In addition, hydrogen is separated from the combined effluent and provided to oxygenate synthesis system 11 via conduit 23. Optionally, the hydrogen may also be combined with the synthesis gas in conduit 9, prior to entering oxygenate synthesis system 11. The ethylene is retrieved separately from workup section 21 and provided via conduit 25 to ethylene oxidation system 27, which comprises an oxygenation zone for oxidising ethylene to ethylene oxide. Oxygen is provided to ethylene oxidation system 27 via conduit 29. From ethylene oxide system 27, ethylene oxide is retrieved via conduit 31 and provided to ethylene oxide hydrolysis system 33, which comprises an ethylene oxide hydrolysis zone, wherein ethylene oxide is hydrolysed to MEG. Water is provided to ethylene oxide hydrolysis system 33 via conduit 35. Ethylene oxidation system 27 and ethylene oxide hydrolysis system 33 are comprised in MEG synthesis system 37. From MEG synthesis system 37, a MEG-comprising effluent is retrieved via conduit 39 and carbon dioxide via conduit 41. The carbon dioxide is provided via conduit 41 to conduit 9 and mixed with the synthesis gas.

EXAMPLES

The invention is illustrated by the following non-limiting calculated examples.

Example 1

In the Examples, several options of implementing the present invention are compared with comparative examples, by means of model calculations. As basis for Examples 1a to g, a model integrated OTO/ethane cracker process was taken. In Table 1, an overview is provided of the feed input and the calculated products.

Calculations were done using a Spyro based model for modelling of cracker operation combined with a proprietary model for modelling the OTO conversion. The key input to the models was as follows:

Cracking:

Steam to ethane ratio is 0.35 wt %. USC coil is used for the Spyro calculations. Calculated at a coil outlet pressure of 1.77 bar absolute, at 65% ethane conversion and a residence time of 0.24 seconds.

OTO Conversion:

MeOH 5012 t/d is fed to the OTO reactor together with 1384 t/d of recycled and superheated steam and 1775 t/d of recycled C4 stream. The model was calibrated on small-scale experiments conducted to determine product distributions for single-pass OTO conversions. Therein, all components that were fed to the OTO reactor have been evaporated and heated such that the temperature in the reactor is controlled between 550-600° C. The pressure in the reactor is 2 bar absolute. The OTO catalyst is fluidized in the reaction medium under the condition that the weight hourly space velocity (WHSV) is 4-10 $h^{-1}$, whereby WHSV is defined as the total weight of the feed flow over the catalyst weight per hour. The following catalyst was used: Composition and preparation: 32 wt % ZSM-23 SAR 46, 8 wt % ZSM-5 SAR 280, 36 wt % kaolin, 24 wt % silica sol, and, after calcination of the ammonium form of the spray dried particle, 1.5 wt % P was introduced by $H_3PO_4$ impregnation. The catalyst was again calcined at 550° C. The steam and C4 recycle streams are excluded from the product composition tables.

Part of the obtained ethylene is converted into MEG. The oxidation of ethylene to ethylene oxide is assumed to be 80% selective, i.e. 80% of the ethylene is converted to ethylene oxide and 20% is converted to carbon dioxide. The selectivity of the ethylene oxide is assumed to be 100% for ease of calculation. For the same reason the conversion of ethylene and ethylene oxide is assumed to be 100%.

The methanol provided to the OTO process (approximately 5000 t/d, see Table 1) is synthesised using at least part of the carbon dioxide ex. EO or in this specific example carbon dioxide from the MEG zone, i.e. carbon dioxide ex. MEG.

The feed containing hydrogen is prepared by combining synthesis gas obtained from one or more synthesis gas producing processes and optionally hydrogen ex. cracker. The yields of methanol are calculated by an Aspen model. To keep the inert concentration of about 40 wt % in the synthesis gas recycle, the amount of purge stream from the recycle is adjusted.

Both hydrogen ex. cracker and carbon dioxide ex. MEG synthesis are taken as 99.9+% pure. Instead of the hydrogen ex. cracker, it is also possible to use the hydrogen obtained from the combined effluent. This will have the effect that less hydrogen needs to be provided externally, and thus less synthesis gas needs to be provided for the production of the methanol.

Natural gas composition is 94.3 mol % $CH_4$, 0.6 mol % $C_2H_6$, 4.6 mol % $N_2$, 0.4 mol % $CO_2$, and 0.1 mol % Ar, based on the total number of moles in the natural gas stream.

The used synthesis gases were:

Synthesis gas from a non-catalytic partial oxidation of natural gas (Shell gasification process). The SGP syngas comprised 61.2 mol % hydrogen, 34.0 mol % carbon monoxide, 2.1 mol % carbon dioxide and 2.5 mol % inerts ($N_2$, Ar and $CH_4$), based on the total number of moles in the SGP syngas.

Synthesis gas from an auto-thermal reforming of natural gas (ATR). The ATR syngas comprised 65.5 mol % hydrogen, 26.7 mol % carbon monoxide, 6.4 mol % carbon dioxide and 1.7 mol % inerts ($N_2$, Ar and $CH_4$), based on the total number of moles in the ATR syngas.

A mixture of synthesis gas from a steam methane reforming (SMR) and a SGP synthesis gas. The mixture comprised 65.8 mol % hydrogen, 25.6 mol % carbon monoxide, 4.4 mol % carbon dioxide and 3.8 mol % inertS ($N_2$, Ar and $CH_4$), based on the total number of moles in the mixture of syngas.

Table 2a provides an overview of the feed, i.e. ethylene, oxygen and water, provided to the MEG synthesis.

Table 2b provides an overview of the feed, i.e. carbon dioxide ex. MEG and the feed containing hydrogen, provided to the methanol synthesis.

Table 2c provides an overview of the feed composition provided to the methanol synthesis.

Table 3 provides an overview of the feedstock, i.e. natural gas, oxygen and water, required to produce the synthesis gas.

Table 4 shows the methanol production based on waste carbon dioxide.

Experiment 1a

Not According to the Invention

The methanol feed to the OTO process is synthesised from a mixture of SGP and SMR synthesis gas. 2949 ton/day of natural gas is required to produce sufficient methanol.

Experiment 1b

Not According to the Invention

The methanol feed to the OTO process is synthesised from a mixture of part of the hydrogen ex. cracker and SGP synthesis gas. 2722 ton/day of natural gas is required produce sufficient methanol.

Furthermore, inert ($N_2$, Ar and $CH_4$) concentration in the feed to the methanol synthesis are reduced, compared to the levels seen in experiment 1a, due to dilution of the SGP synthesis gas with hydrogen obtained from the ethane cracker.

Experiment 1c

Approximately 581 ton/day of ethylene is provided, with separately oxygen and water, to the MEG zone and is converted into MEG and carbon dioxide.

The methanol feed to the OTO process is synthesised from a mixture of carbon dioxide ex. MEG, hydrogen ex. cracker and SGP synthesis gas. By addition of pure carbon dioxide from the MEG production unit the carbon dioxide content is increased to 3.3 mol %, based on the total feed to the methanol synthesis. The natural gas consumption for producing the methanol has decreased by 12 wt % and 5 wt % respectively based on the natural gas required for producing the methanol in Experiment 1a and 1b. In addition, 255 ton/day of methanol is produced based on waste carbon dioxide, i.e. carbon dioxide ex. MEG, i.e. not produced as part of the process to prepare synthesis gas, which would need to be sequestered or otherwise captured and stored. As a result, the carbon dioxide penalty of the process is reduced.

Again, inert ($N_2$, Ar and $CH_4$) concentrations are further lowered.

Experiment 1d

Approximately 2520 ton/day of ethylene is provided, with separately oxygen and water, to the MEG zone and is converted into MEG and carbon dioxide.

The methanol feed to the OTO process is synthesised from a mixture of carbon dioxide ex. MEG, hydrogen ex. cracker, SGP synthesis gas and the addition of additional hydrogen for instance from a second or further ethane cracker unit, or styrene production unit. By addition of pure carbon dioxide from the MEG production unit the carbon dioxide content is increased to 7.9 mol %%, based on the total feed to the methanol synthesis. The natural gas consumption for producing the methanol has decreased by 27 wt % and 21 wt % respectively based on the natural gas required for producing the methanol in Experiment 1a and 1b. In addition 1062 ton/day of methanol is produced based on waste carbon dioxide, i.e. carbon dioxide ex. MEG.

Again, inert ($N_2$, Ar and $CH_4$) concentrations are further lowered.

Experiment 1e

Not According to the Invention

The methanol feed to the OTO process is synthesised from a mixture of part of the hydrogen ex. cracker and ATR synthesis gas. 2933 ton/day of natural gas is required to produce sufficient methanol.

Experiment 1f

Approximately 633 ton/day of ethylene is provided, with separately oxygen and water, to the MEG zone and is converted into MEG and carbon dioxide.

The methanol feed to the OTO process is synthesised from a mixture of carbon dioxide ex. MEG, hydrogen ex. cracker and ATR synthesis gas. By addition of pure carbon dioxide from the MEG production unit the carbon dioxide content is increased to 7.1 mol %, based on the total feed to the methanol synthesis. The natural gas consumption for producing the methanol has decreased by 6 wt % and 5 wt % respectively based on the natural gas required for producing the methanol in Experiments 1a and 1e. In addition 273 ton/day of methanol is produced based on waste carbon dioxide, i.e. carbon dioxide ex. MEG. As a result, the carbon dioxide penalty of the process is reduced.

Again, inert ($N_2$, Ar and $CH_4$) concentrations are further lowered.

Experiment 1 g

Approximately 1010 ton/day of ethylene is provided, with separately oxygen and water, to the MEG zone and is converted into MEG and carbon dioxide.

The methanol feed to the OTO process is synthesised from a mixture of carbon dioxide ex. MEG, hydrogen ex. cracker and ATR synthesis gas. By addition of pure carbon dioxide from the MEG production unit the carbon dioxide content is increased to 7.9 mol %, based on the total feed to the methanol synthesis. The natural gas consumption for producing the methanol has decreased by 9 wt % and 8.9 wt % respectively based on the natural gas required for producing the methanol in Experiment 1a and 1e. In addition, 443 ton/day of methanol is produced based on waste carbon dioxide. As a result, the carbon dioxide penalty of the process is reduced.

Again, inert ($N_2$, Ar and $CH_4$) concentrations are further lowered.

TABLE 1

|  | OTO $10^3$ kg/day | Ethane cracker $10^3$ kg/day | Integrated OTO/ethane cracker $10^3$ kg/day |
|---|---|---|---|
| Feed: |  |  |  |
| Methanol | 5012 |  | 5012 |
| Ethane |  | 2755 | 2755 |

TABLE 1-continued

|  | OTO $10^3$ kg/day | Ethane cracker $10^3$ kg/day | Integrated OTO/ethane cracker $10^3$ kg/day |
|---|---|---|---|
| Products: |  |  |  |
| Ethylene | 512 | 2187 | 2713 |
| Propylene | 1275 | 50 | 1325 |
| Ethane | 17 |  |  |
| propane | 48 | 19 | 67 |
| >C3 | 318 | 135 | 453 |
| Fuel gas | 98 | 197 | 280 |
| $H_2O$ | 2710 | −83 | 2627 |
| Hydrogen | 17 | 168 | 186** |

*based on $CH_2$ in the feed

**including hydrogen obtained by recycling ethane in the effluent of the OTO to the ethane cracker.

TABLE 2a

| Exp. | Feed to MEG $10^3$ kg/day | | | Product $10^3$ kg/day | |
|---|---|---|---|---|---|
|  | $C_2H_4$ | $O_2$ | $H_2O$ | MEG | $CO_2$ ex. MEG |
| 1a | — | — | — | — | — |
| 1b | — | — | — | — | — |
| 1c | 581 | 664 | 149 | 1029 | 365 |
| 1d | 2520 | 2880 | 648 | 4464 | 1584 |
| 1e | — | 0 | — | — | — |
| 1f | 633 | 724 | 163 | 1122 | 398 |
| 1g | 1010 | 1155 | 260 | 1790 | 635 |

TABLE 2b

| Exp. | Feed $10^3$ kg/day | | | Product $10^3$ kg/day |
|---|---|---|---|---|
|  | $H_2$ ex. cracker | Synthesis gas | $CO_2$ ex MEG | Methanol |
| 1a | — | 2236 (ex. SMR) 3883 (ex. SGP) | — | 5000 |
| 1b | 129 | 5488 (ex. SGP) | — | 5000 |
| 1c | 173 | 5208 (ex. SGP) | 365 | 5000 |
| 1d | 321 | 4322 (ex. SGP) | 1584 | 5000 |
| 1e | 82 | 5837 (ex. ATR) | — | 5000 |
| 1f | 134 | 5518 (ex. ATR) | 398 | 5000 |
| 1g | 165 | 5320 (ex. ATR) | 635 | 5000 |

TABLE 2c

| Exp. | Composition mol %* | | | | | Molar ratio |
|---|---|---|---|---|---|---|
|  | $H_2$ | CO | $CO_2$ | $N_2$, AR, $CH_4$ | $H_2O$ |  |
| 1a | 65.8 | 25.6 | 4.4 | 3.8 | 0.2 | 2.05 |
| 1b | 66.1 | 29.7 | 1.8 | 2.2 | 0.2 | 2.04 |
| 1c | 66.7 | 27.8 | 3.3 | 2.0 | 0.2 | 2.04 |
| 1d | 68.5 | 21.8 | 8.0 | 1.6 | 0.1 | 2.03 |
| 1e | 68.1 | 24.6 | 5.9 | 1.4 | >0.1 | 2.04 |
| 1f | 68.6 | 22.9 | 7.2 | 1.3 | >0.1 | 2.04 |
| 1g | 69.0 | 21.9 | 7.9 | 1.2 | >0.1 | 2.05 |

*Based on the total number of moles in the feed

**molar ratio = (#mol $H_2$ − #mol $CO_2$)/(#mol CO + #mol $CO_2$)

TABLE 3

| Exp. | Feed 10³ kg/day Natural gas | O₂ | H₂O | Total feedstock 10³ kg/day |
|---|---|---|---|---|
| 1a | 2949 | 2291 | 1210 | 6450 |
| 1b | 2722 | 3239 | 0* | 5961 |
| 1c | 2583 | 3074 | 0* | 5657 |
| 1d | 2144 | 2551 | 0* | 4695 |
| 1e | 2933 | 3109 | 1691 | 7733 |
| 1f | 2773 | 2939 | 1599 | 7311 |
| 1g | 2674 | 2834 | 1541 | 7049 |

*In principle no water is added.

TABLE 4

| Exp. | Feed 10³ kg/day CO₂ ex MEG | Product 10³ kg/day Methanol | Methanol from CO₂ ex. MEG |
|---|---|---|---|
| 1a | — | 5000 | |
| 1b | — | 5000 | |
| 1c | 365 | 5000 | 255 |
| 1d | 1584 | 5000 | 1062 |
| 1e | — | 5000 | |
| 1f | 398 | 5000 | 273 |
| 1g | 635 | 5000 | 443 |

By using a synthesis gas such as SGP synthesis gas, which comprises relatively low amounts of carbon dioxide it is possible to capture significant amounts of waste carbon dioxide in the form of methanol, ethylene, MEG or products derived thereof. In addition, by using a synthesis gas which is produced by a process in which in principle no or only little water is used, such as a non-catalytic partial oxidation process, water consumption is significantly lowered.

What is claimed is:

1. A process for producing ethylene oxide, comprising:
   a. cracking an ethane-comprising feed in a cracking zone under cracking conditions to obtain olefins including at least ethylene and hydrogen;
   b. converting an oxygenate feedstock in an oxygenate-to-olefin zone to obtain olefins, including at least ethylene; and
   c. providing at least part of the ethylene obtained in step (a) and (b) to an ethylene oxidation zone together with a feed containing oxygen and oxidising ethylene to obtain at least ethylene oxide and carbon dioxide;
   wherein at least part of the oxygenate feedstock is obtained by providing carbon dioxide obtained in step (c) and a feed containing hydrogen to an oxygenate synthesis zone and synthesising oxygenates, which feed containing hydrogen comprises hydrogen obtained in step (a).

2. A process according to claim 1, wherein in step (a) a cracking zone effluent comprising ethylene and hydrogen is obtained and in step (b) an oxygenate-to-olefin zone effluent comprising olefins and hydrogen is obtained and at least part of the hydrogen in the feed containing hydrogen is obtained by combining at least part of the cracking zone effluent and at least part of oxygenate-to-olefin zone effluent and separating hydrogen from the combined effluent.

3. A process according to claim 1, wherein the olefins obtained in step a) and/or b) further include propylene.

4. A process according to claim 1, wherein the feed containing hydrogen also comprises carbon monoxide.

5. A process according to claim 1, comprising providing carbon dioxide and hydrogen, to the oxygenate synthesis zone in a molar ratio of in the range of from 2.0 to 3.0.

6. A process according to claim 5, wherein carbon dioxide is present in a concentration in the range of from 0.1 to 25 mol %, based on the total number of moles carbon dioxide, hydrogen, and carbon monoxide.

7. A process according to claim 1, comprising combining at least part of the olefins obtained in step a) and b) in one stream.

8. A process according to claim 1, wherein the feed containing hydrogen comprises a synthesis gas.

9. A process according to claim 1, wherein the carbon dioxide is obtained as a stream comprising carbon dioxide, which further comprises chlorine and the stream comprising carbon dioxide is treated to remove chlorine prior to providing the stream comprising carbon dioxide to the oxygenate synthesis zone.

10. A process according to claim 1, comprising:
   i) providing a feed comprising methane and ethane;
   ii) separating the feed into at least a methane-comprising feed and an ethane-comprising feed;
   iii) providing at least part the methane-comprising feed to a process for preparing synthesis gas to obtain a synthesis gas; and
   iv) providing at least part of the ethane to the cracking zone and at least part of the synthesis gas to the oxygenate synthesis zone.

11. A process according to claim 10, wherein the feed comprising methane and ethane is natural gas or associated gas.

12. A process according to claim 10, wherein the feed comprising methane and ethane comprises in the range of 1 to 20 mol % of ethane, based on the total feed.

* * * * *